United States Patent [19]

Bojar et al.

[11] Patent Number: 4,827,552
[45] Date of Patent: May 9, 1989

[54] ROTARY ELECTRIC TOOTHBRUSH

[75] Inventors: James A. Bojar, Wauwatosa; Richard J. Shaw, Brookfield, both of Wis.

[73] Assignee: Better Health Concepts, Inc., Milwaukee, Wis.

[21] Appl. No.: 167,800

[22] Filed: Mar. 14, 1988

[51] Int. Cl.⁴ .......................................... A46B 13/02
[52] U.S. Cl. ....................................................... 15/28
[58] Field of Search ..................... 15/23, 24, 28, 29; 433/124, 125, 131, 133

[56] References Cited

U.S. PATENT DOCUMENTS

| | | | |
|---|---|---|---|
| 1,833,967 | 12/1931 | Groff, Jr. | 15/23 |
| 1,947,324 | 2/1934 | Zerbee | 15/28 |
| 2,124,145 | 7/1938 | Merkel, Jr. | 15/23 |
| 2,140,307 | 12/1938 | Belaschk et al. | 15/28 |
| 2,278,095 | 3/1942 | Rogers | 15/28 |
| 2,808,602 | 10/1957 | Gregoire | 15/28 |
| 2,916,752 | 12/1959 | Baker | 15/28 |
| 3,195,537 | 7/1965 | Blasi | 15/28 |
| 3,220,039 | 11/1965 | Dayton | 15/28 |
| 3,822,432 | 7/1974 | Skinner | 15/23 |
| 4,079,517 | 3/1978 | Zacharia | 15/28 |
| 4,619,009 | 10/1986 | Rosenstatter | 15/28 |

FOREIGN PATENT DOCUMENTS

| | | | |
|---|---|---|---|
| 3341465 | 5/1985 | Fed. Rep. of Germany | 15/28 |
| 452961 | 9/1936 | United Kingdom | 15/28 |

Primary Examiner—Edward L. Roberts
Attorney, Agent, or Firm—Robert T. Johnson

[57] ABSTRACT

Disclosure is made of an invention for a rotary electric toothbrush, of a head segment demountably attached to a body segment, and the head segment having a gear train in the top of the head segment such that the angle between the center line of the end brush and the drive shaft can be from 70° to 90° and a rechargeable battery and motor is contained in the body segment. The head segment is mounted on the body segment by means of raised buttons of the body segment fitting in dimples of the head segment.

4 Claims, 4 Drawing Sheets

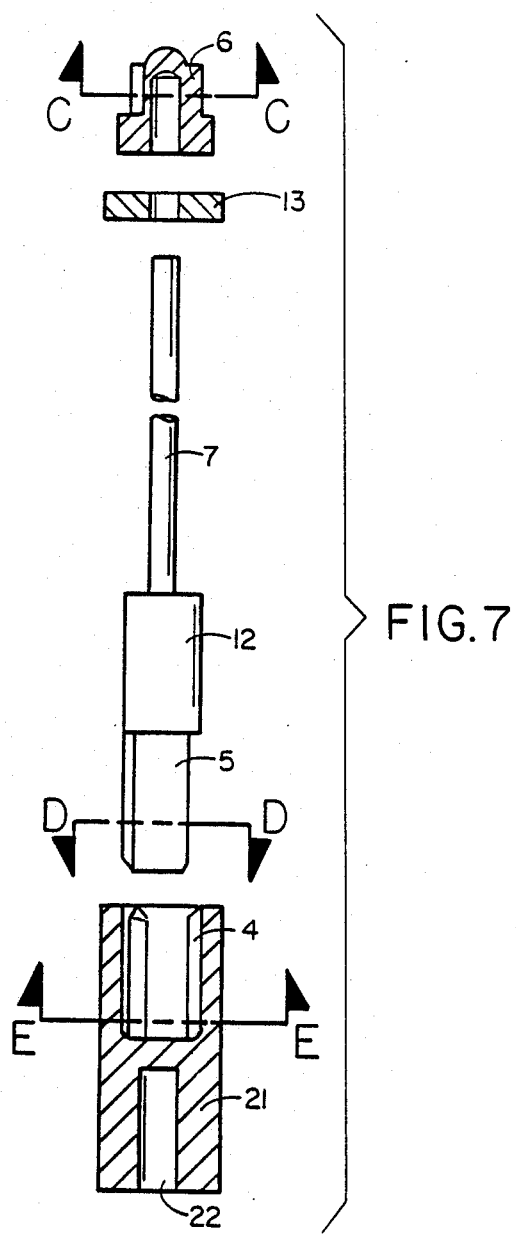
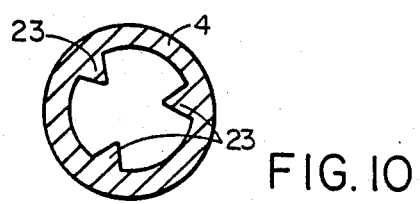
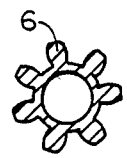
FIG. 8
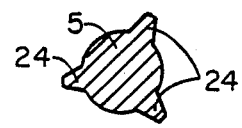
FIG. 9
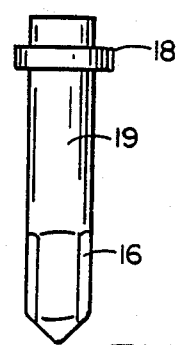
FIG. 13

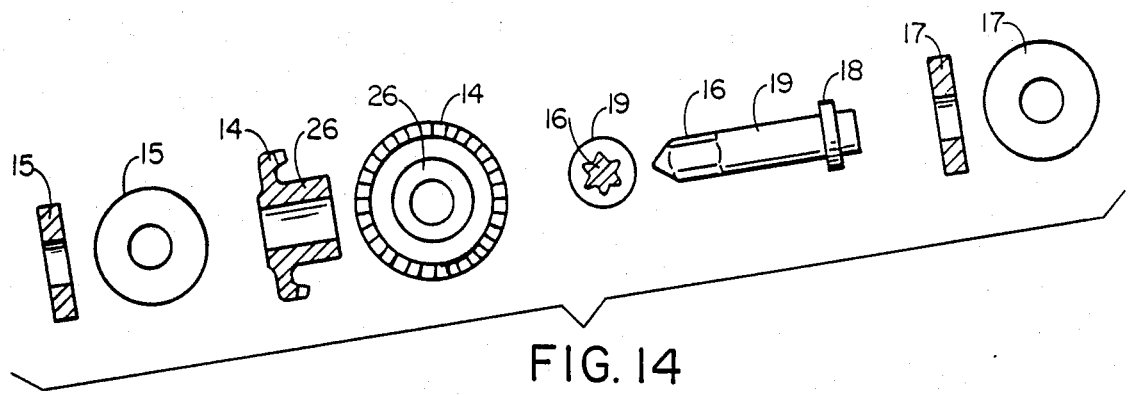
FIG. 14
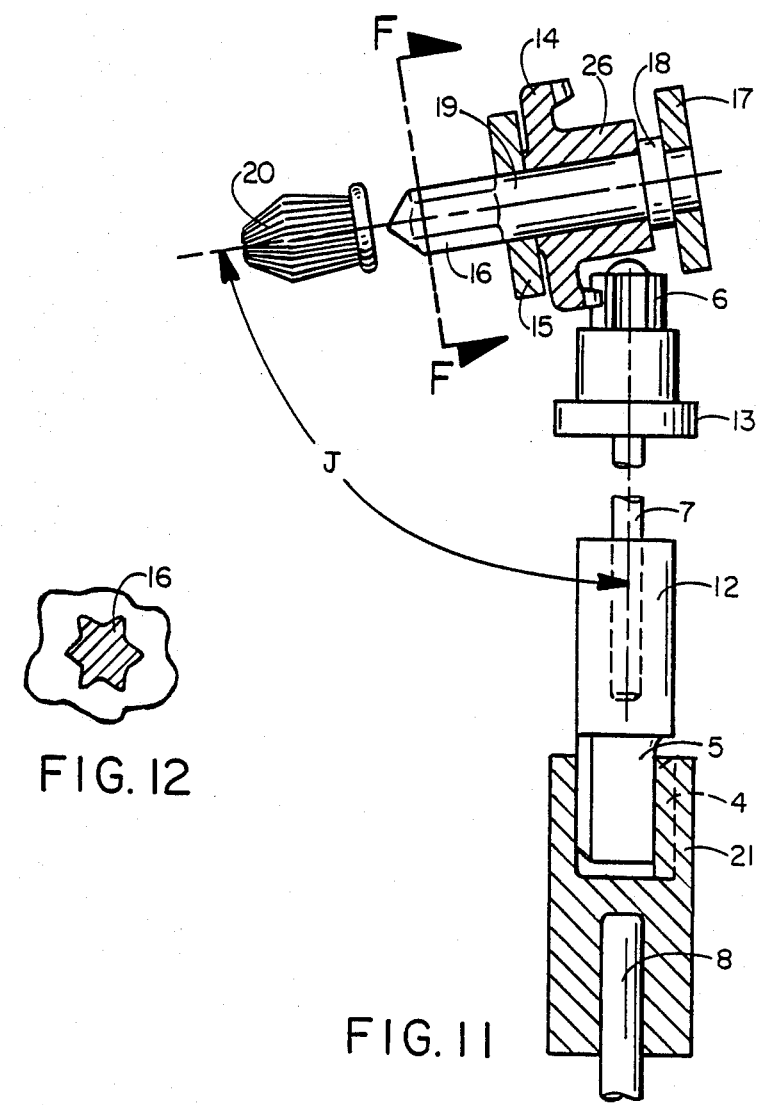
FIG. 12
FIG. 11

ROTARY ELECTRIC TOOTHBRUSH

INTRODUCTION

To date there have been electric toothbrushes of various types, each of which filled a specific need, such as gum massage, interstitial cleaning, or general tooth cleaning.

EXPLANATION OF INVENTION

This invention pertains to an electric powered toothbrush with a gear reduction head to allow a fixed brush angle from the power drive shaft of from 70° to 90°.

Heretofore the gear reduction drive from the motor to the drive shaft has, by necessity, been at the motor drive take off, not in a removable head. This disclosure of invention includes means of having the gear reduction drive at the top of the head section of the electric toothbrush apparatus.

This present invention is to disclose a rotary electric toothbrush in which the end brush bristle extends outward from the head at a fixed angle of 70° to 90° and a speed reducing gear is located in the head, and further the head portion is readily removable from the main body portion. By having a removable head section, each user of this electric toothbrush can have their own toothbrush head and brush to thus prevent spread of germs from user to user and further by having removable head sections each user can have their own fixed specific angle of 70°–90°.

An object of this invention is to disclose a rotary electric toothbrush comprising a head segment and a gear train in the top of the head segment and the gear train is comprised of a drive gear attached to a drive shaft in the head segment and a crown gear meshing with the drive gear and the hub of the crown gear fitting over and attached to a driven shaft, and the driven shaft mounted on bearings in the top of the head segment housing and the driven shaft mounted at an angle of 70° to 90° as measured from the drive shaft of the head segment and the driven shaft having a splined end and an end brush mounted on the splined end of the driven shaft, and the head section demountably attached to the body segment by buttons of the body segment fitting in dimples of the head section.

Another object of this invention is to disclose a rotary electric toothbrush wherein a removable head section is readily separated from the drive segment of the toothbrush.

Another object of this invention is to disclose a rotary electric toothbrush having a removable head segment.

Another object of this invention is to disclose a rotary electric toothbrush having a gear section in the removable head segment.

Another object of this invention is to disclose a rotary electric toothbrush having a rotary driven brush shaft extending from the head at a fixed angle of from 70° to 90° from the center line of drive shaft.

By having the gear section in the top of head segment, a different gear mechanism is changed each time a new or different head segment is attached to the power drive segment. This arrangement then insures longer life of the drive section and gear reduction is readily changed with replacement of the head section.

The gear drive in the top of the head segment may also include a gear reduction train.

Another object is to disclose a male splined section on the driven shaft of the head segment fitting into a female inner splined section of power drive shaft.

PRIOR ART BACKGROUND

U.S. Pat. No. 2,278,095 for Electrical Toothbrush Issued 3/31/42. This patent discloses a right angled brush mount on electrically driven drive shaft. Note the brush stem 20 is held by latch member 25 engaging notch 26.

U.S. Pat. No. 2,808,602 for Rotary Brush Issued 10/8/57. This patent discloses a rotary brush suitable for a toothbrush. The brush is at a right angle and the brush is held by spring 28 in groove 29.

U.S. Pat. No. 2,916,752 for Rotary Tooth Brush Issued 12/15/59. Disclosure is made in this patent of a friction fit of brush stem in drive shaft 12 and having a clutch 17 for variable speed.

U.S. Pat. No. 3,220,039 for Motor Driven Tooth Brush Issued 11/30/65. Disclosure is made in this patent of a removable head brush, and battery powered motor.

U.S. Pat. No. 3,757,419 for Portable Tooth Cleaner Issued 9/11/73. This patent discloses flexible torsion cable as a drive for rotary brush head.

U.S. Pat. No. 3,822,432 for Dental Hygiene Appliance Issued 7/9/74. Disclosure is made in this patent of a flexible drive shaft in a curved tubular extension, and driven by a battery.

U.S. Pat. No. 4,079,517 for Home Prophylasis Unit Issued 3/21/78. Disclosure is made in this patent of a water tight seal of the mechanism.

U.S. Pat. No. 4,420,851 for Mechanized Tooth Brush Having Movement In Two Planes. Issued 12/20/83. This patent discloses an electric tooth brush having rotary and longitudinal motion.

U.S. Pat. No. 4,619,009 for Tooth Cleaning Apparatus Issued 10/28/86. This patent resulted from P.C.T. (see Ex. A) application of Rosenstatter of Austria, abstract of which is attached hereto. Disclosure is made in this patent of a right angle head and brush mount and includes means to supply liquid (water) to brush head.

BRIEF DESCRIPTION OF DRAWINGS

FIG. 7—Elevation view of sections comprising the drive shaft and drive gear.

FIG. 8—Cross section view of drive gear.

FIG. 9—Cross section view of male end of drive coupling shaft.

FIG. 10—Cross section view of female end of drive coupling shaft.

FIG. 11—Elevation view of component parts of assembly of drive shaft and gear reduction arrangement in head of the toothbrush.

FIG. 12—Cross section view of spline shaft.

FIG. 13—Lengthwise view of spline head and shaft.

FIG. 14—Expanded component assembly of drive reduction crown gear and spline head and shaft.

DETAILED DESCRIPTION OF DRAWINGS DISCLOSING INVENTION

Figure 4:
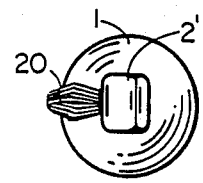
FIG. 4—End plan view of brush mount head of electric powered rotary toothbrush.
Figure 1:
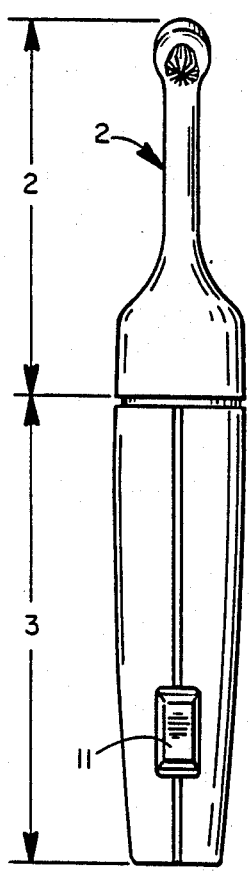
FIG. 1—Elevation view of front (switch side) of electric powered rotary toothbrush.
Figure 2:
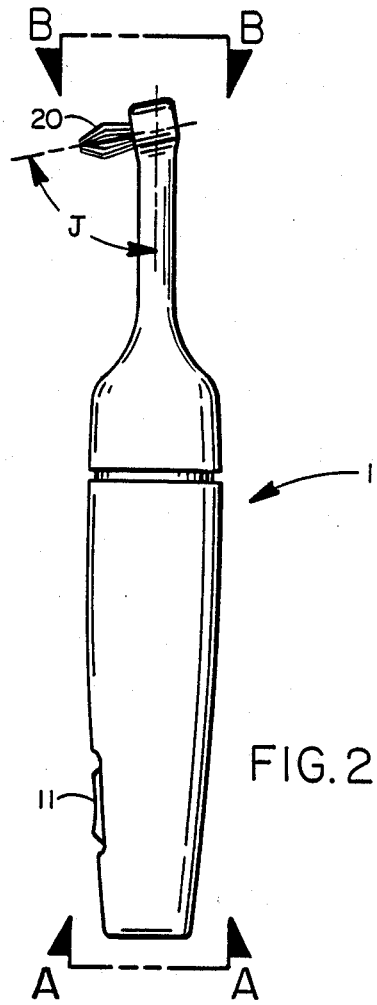
FIG. 2—Elevation side view of side of electric powered rotary toothbrush.
Figure 3:
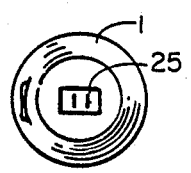
FIG. 3—End plan view of bottom of electric powered rotary toothbrush.

FIG. 1—Elevation view of front (switch side) of electric powered rotary toothbrush.
- 1—Assembled electric powered rotary toothbrush
- 2—Head section
- 3—Body of drive section
- 11—On-off switch FIG. 2—Elevation side view of side of electric powered rotary toothbrush.
- 1—Assembled electric powered rotary toothbrush
- 2—Head section
- 3—Body of drive section
- 11—On-off switch
- J—Angle of brush center line to center line of drive shaft FIG. 3—End plan view of electric powered rotary toothbrush. (Section A—A)
- 1—Plan view of bottom end
- 25—Receptacle for connection to recharging leads FIG. 4—End plan view of brush mount head of electric powered rotary toothbrush. (Section B—B)
- 1—Plan view of brush mounted in head
- 2—Top of head section
- 20—Rotary end brush FIG. 5—Inner assembly elevation view of separate sections of this toothbrush shown in alignment for assembly to complete the electric powered rotary toothbrush.
- 2—Removable head section shown separated from drive section
- 3—Drive section of toothbrush including connector 21
- 4—Female splined end of connector 21 joining driven and drive shafts
- 5—Self aligning male splined connector end of driven shaft connector
- 7—Driven shaft
- 8—Drive motor shaft
- 9—Drive motor
- 10—Rechargeable battery pack
- 11—On-off switch
- 12—Driven shaft connector
- 20—Rotary end brush
- 21—Double female connector attached to electric motor shaft
- 25—Receptacle for connection to recharger leads
- 27—Leads from battery recharger
- 28—Battery recharger
- 29—Dimples
- 30—Raised buttons
- 31—Electric connection wires from switch and battery
- 32—Electric connection wires from charger to battery
- J—Angle of brush drive center line from center line of drive shaft FIG. 6—Inner assembly elevation view of workings of electric powered rotary toothbrush.
- 2—Removable head section
- 3—Drive section of toothbrush
- 4—Connector from drive motor shaft to driven shaft
- 5—Self aligning male connector end of driven connector shaft
- 7—Driven shaft
- 8—Drive motor shaft
- 9—Drive motor
- 10—Rechargeable battery pack
- 11—On-off switch
- 12—Driven shaft connector
- 20—Rotary end brush
- 21—Double female connector attached to electric motor shaft
- 25—Receptacle for connection to recharger leads
- 27—Leads from battery recharger
- 28—Battery recharger
- 29—Dimples
- 30—Raised buttons
- 31—Connection wires from switch and battery
- 32—Electric connection wires from charger to battery
- J—Angle of brush drive center line from center line of drive shaft FIG. 7—Elevation view of sections comprising the drive shaft and drive gear.
- 4—Female end of connector 11 joining driven and drive shafts
- 5—Self aligning male connector end of driven shaft connector
- 6—Drive head gear
- 7—Driven shaft
- 12—Driven shaft connector
- 13—Bearing guide for drive shaft
- 21—Double female connector from drive shaft motor to
- 22—Driven shaft
- 23—Inward extending splines FIG. 8—Cross section view of drive gear (Section C—C).
- 6—Cross section of drive gear teeth FIG. 9—Cross section view of male end of drive coupling shaft (Section D—D)
- 5—Cross section of self aligning male connector on driven shaft FIG. 10—Cross section view of female end of drive coupling shaft (Section E—E).
- 4—Cross section view of female end of connector 11 joining driven and drive shafts FIG. 11—Elevation view of component parts of assembly of drive shaft and gear reduction arrangement in head of the toothbrush.
- 4—Female end of connector 11 joining driven and drive shafts
- 5—Self aligning male connector end of driven shaft connector
- 6—Drive head gear
- 7—Drive shaft
- 8—Drive motor shaft
- 12—Driven shaft connector
- 14—Crown gear
- 15—Bearing mount
- 16—Spline section of shaft 19
- 17—Bearing mount
- 18—Shoulder on brush drive shaft
- 19—Brush drive shaft
- 20—Rotary brush
- 15—Bearing for crown gear
- J—Angle of brush center line from center line of drive shaft
- 26—Crown gear hub FIG. 12—Cross section view of spline shaft (Section F—F).

16—Cross section of spline segment
FIG. 13—Lengthwise view of spline head and shaft.
16—Spline section of shaft 19
19—Brush drive shaft
18—Shoulder on brush drive shaft
FIG. 14—Expanded component assembly of driven reduction crown gear and spline head and shaft.
14—Crown gear
15—Bearing for crown gear
16—Spline section of shaft 19
17—Bearing on shoulder of shaft
18—Shoulder on brush drive shaft
19—Brush drive shaft
26—Hub of crown gear

DETAILED DESCRIPTION OF INVENTION

The electric toothbrush of this invention comprises two major components, 2 head section and 3 body of drive section, assembled together as an assembled electric powered rotary toothbrush 1. The 3 body of drive section contains on-off switch 11 connected from rechargeable battery pack 10 to drive motor 9, through suitable wiring well known in the art.

Connector 21 is attached to drive motor shaft 8, and on the end opposite the connector 21 attached to drive motor shaft 8, is a female end of connector 21 joining driven and drive shafts 4. A self aligning male connector end of driven connector shaft 5, is firmly attached driven shaft 7.

Referring now to FIG. 7, connector 21 comprises female opening 22 into which drive motor shaft 8 is permanently attached. The female opening 4 of connector 21 consists of inward extending splines 23. The number of splines 23, is shown as three in number.

The head section 2, comprises a housing 25, and mounted therein on driven shaft 7 is connector 12 comprising a male connector end of driven shaft connector 5, comprised of outward extending splines 24, three in number and on assembly of head section 2 on body of drive section 3 fitting in female end 4 of connector 21, having inward extending splines.

Driven shaft 7 extends from driven shaft connector 12, through 13, bearing guide for drive shaft to drive head gear 6.

Drive head gear 6 is firmly attached to driven shaft 7, and this drive head gear 6 is mounted to mesh with teeth of crown gear 14 which is firmly attached to brush drive shaft 19. The crown gear 14 attached to brush drive shaft 19 is mounted on bearing mounts 15 and 17. End brush 20 is mounted on spline section 16 of shaft 19. Shoulder 18 on brush drive shaft acts as a spacer between bearing mount 17, and crown gear hub 26.

End brush 20 is mounted on spline section of shaft 19, and because of the spline section there is an interference fit of the end brush 20 on shaft 19.

The angle J is identified as the angle between the center line of brush drive shaft 19 and the center line of driven shaft 7, and the preferred range of this angle J is 70° to 90°, the preferred angle is 80°.

Figure 5:
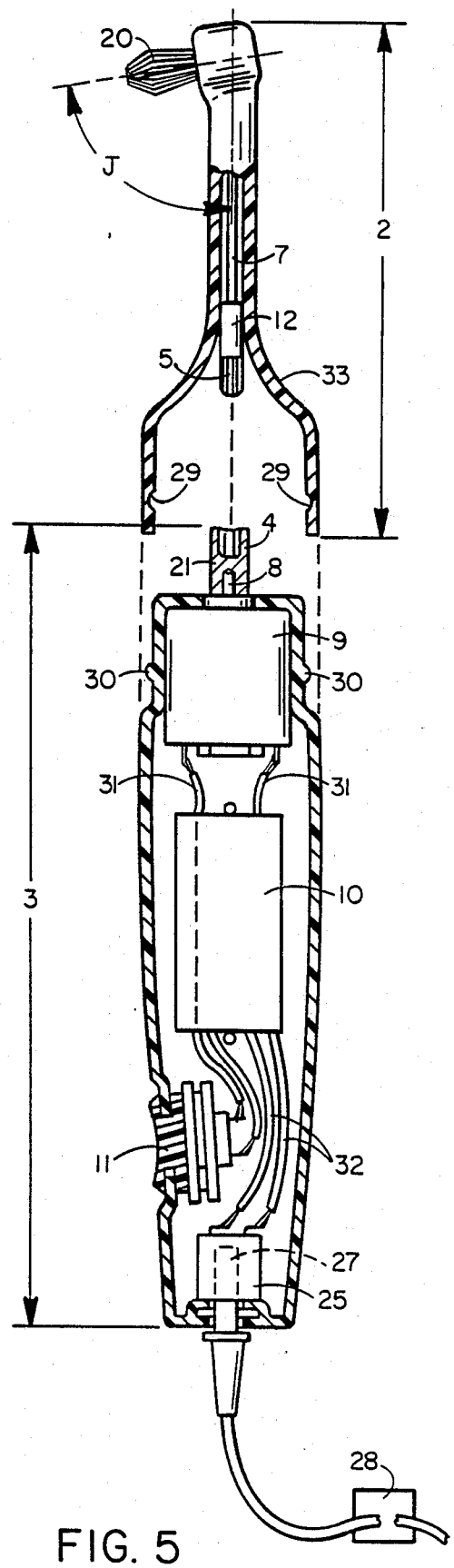
FIG. 5—Inner assembly elevation view of separate sections of this toothbrush shown in alignment for assembly to complete the electric powered rotary toothbrush.

Referring to FIG. 5, legend 3 is the drive body section as indicated on the outside of the toothbrush assembly and includes legend 21 which is a double female connector from electric motor drive shaft to driven shaft.

The hub 26 of crown gear 14 rides against shoulder 18 of brush drive shaft 19.

Figure 6:
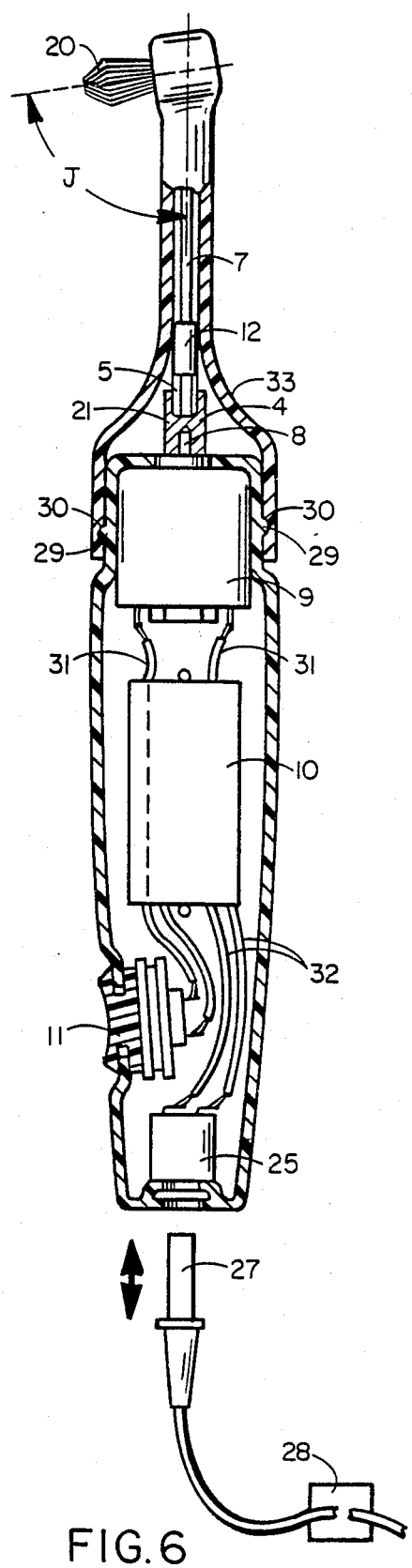
FIG. 6—Inner assembly elevation view of workings of electric powered rotary toothbrush.

The leads from the battery charger 27 and the battery charger 28 and the connection wires 31 from switch and battery and from charger to battery 32 are shown in FIGS. 5 and 6.

As stated above the head segment 2 is demountably attached to the body segment 3 by means of dimples 29 in the inside wall of the housing 33 of the head segment, and these dimples fit over raised buttons 30 on outer surface of body segment 3, fitting into the base of the head segment when the segments 2 and 3 are attached for a complete assembly of this rotary electric toothbrush.

It is to be pointed out that the male splined section 5 having splines 24 on the driven shaft 7 of the head segment 2 is fitted into the female inner splined section 4 of connector 21 attached to power shaft 8 of electric motor. The female inner splines 23 are noted in FIG. 10, while the male splines 24 are shown in FIG. 9, and is part of the whole invention.

The housing for both the removable head section 2 and drive section 3 of this electric toothbrush can be of molded thermoplastic material such as polyethylene, polystyrene or polypropylene, or similar materials.

Having described our invention, we claim:

1. An electric rotary toothbrush driven by a rechargeable battery wherein the improvement comprises:
   a—a head segment and
   b—a gear train in top of said head segment and
   c—said gear train comprised of a drive gear attached to a drive shaft in said top of said head segment and
   d—a crown gear meshing with said drive gear and
   e—the hub of said crown gear fitting over and attached to a driven shaft
   f—said driven shaft mounted on bearings in the top of head segment housing and
   g—said driven shaft mounted at an angle of less than 90° as measured from said driven shaft of head segment
   h—said driven shaft having a splined end and
   i—an end brush mounted on said splined end of said driven shaft, and
   j—said head segment demountably attached to a body segment by means of raised buttons in said body segment meshing with dimples in said head segment and
   k—a male splined section on said drive shaft of said head segment fitting into a female inner splined section of a power drive shaft and
   l—electricial rechargeable power source and electric motor drive in said body segment to actuate said driven shaft in said head segment.

2. An electric rotary toothbrush driven by a rechargeable battery wherein the improvement comprises:
   a—a head segment and
   b—a speed reduction gear train in the top of said head segment
   c—and said speed reduction gear train comprised of a drive gear attached to a drive shaft in said head segment and
   d—a crown gear meshing with said drive gear and the
   e—hub of said crown gear attached to and fitting around a driven shaft at 80° angle between said shafts
   f—and said driven shaft mounted on bearings in the top of said head segment housing and
   g—said driven shaft having a splined end and h—an end brush mounted on said splined end of said driven shaft and i—said head segment demountably attached to a body section by means of raised buttons on said body segment fitting in dimples of the head segment and j—a male splined section on driven shaft of head segment fitting into a female inner splined section of power drive shaft and k—electrical rechargeable power source and an electric motor drive in said body segment l—to actuate said drive shaft.

3. An electric rotary toothbrush driven by a rechargeable battery wherein the improvement comprises:

a—a head segment (2) and b—a gear train in said head segment (2) to attain an angle of 80° between a brush drive shaft (19) and driven shaft (7) in said head segment by means of c—a gear train comprised of a drive gear (6) attached to said driven shaft (7) in said head segment (2) and d—a crown gear (14) meshing with said drive gear (6) and e—the hub of said crown gear (14) fitting over and attached to said brush drive shaft (19) and f—said brush drive shaft (19) mounted in said head segment and g—said brush drive shaft (19) mounted at said angle of 80°, as measured from driven shaft (7) of head segment and h—a spline section (16) of shaft (19) and i—an end brush (20) mounted on said spline section (16) of brush drive shaft 19 and j—said head segment (2) demountably attached to body segment (3) by means of raised buttons (30) in said body segment meshing with dimples (29) in said head segment and k—a male connector end (5) of driven shaft (7) of said head segment fitting into female inner splined section (4) of power drive shaft (8) and l—electrical rechargeable power source, or battery pack (10) and electric drive motor (9) in said body segment (3) to actuate said drive shaft and said driven shaft (7) in said head segment.

4. An electric rotary toothbrush driven by a rechargeable battery wherein the improvement comprises:

a—a head segment and b—a speed reduction gear train in said head segment and c—said speed reduction gear train comprised of a driven gear attached to a driven shaft in said head segment to attain an angle of 80° between a brush drive shaft and driven shaft in said head segment by means of d—a crown gear meshing with said driven gear and the hub of said crown gear attached to and fitting around said brush drive shaft and e—said brush drive shaft mounted on bearings in said head segment housing and f—said brush drive shaft having a splined end and g—and end brush mounted on said splined end of said brush drive shaft and h—said head segment is demountably attached to body drive segment of toothbrush by means of raised buttons on the said body drive segment fitting in dimples of said head segment and i—a male splined section on the driven shaft of said head segment fitting into a female inner splined section of the power drive shaft of said body drive segment and j—electrical rechargeable power source and an electric motor drive in said body drive segment to actuate said drive shaft and k—said brush drive shaft mounted at said angle of 80° from driven shaft of head segment.

* * * * *